Aug. 8, 1944. F. H. HOWARD Plant Pat. 637
ROSE PLANT
Filed Dec. 17, 1943
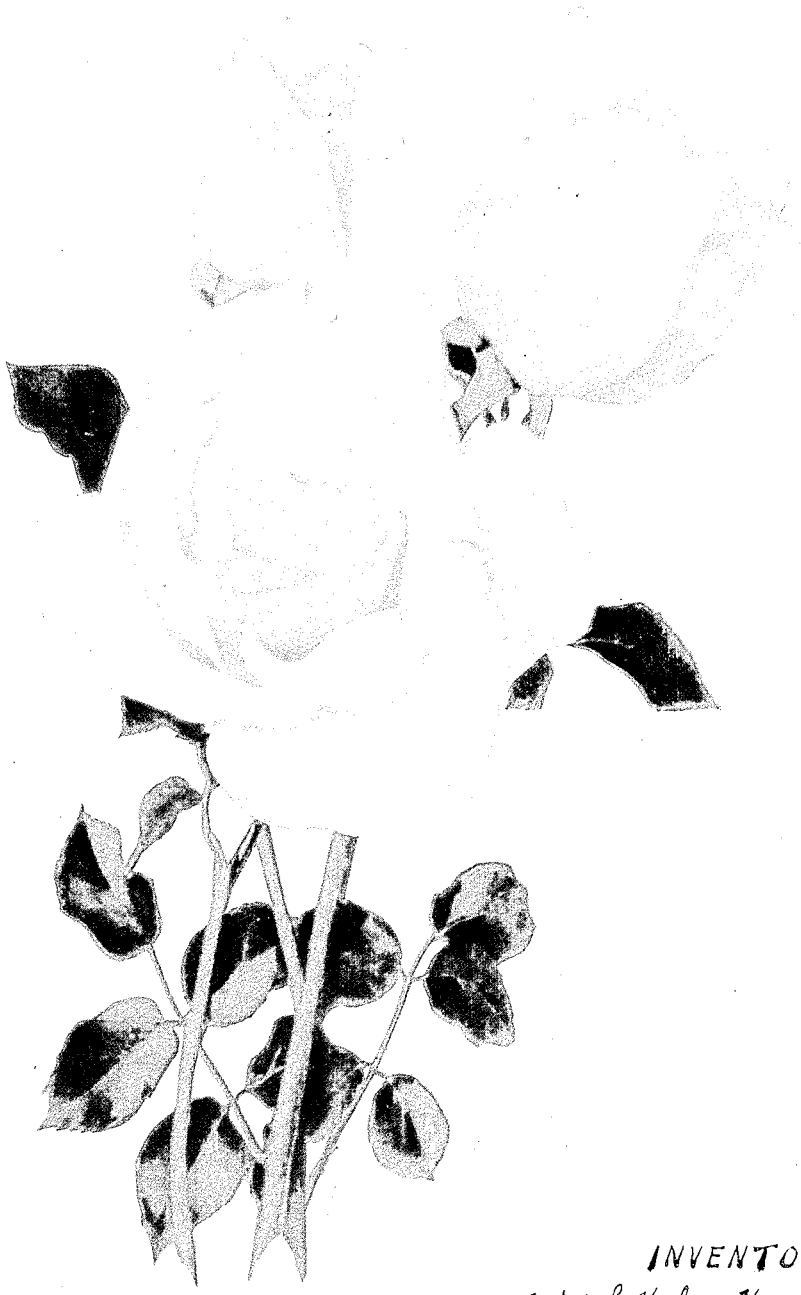
INVENTOR
Frederick Huber Howard
By Orville M. Kile
Plant Pat. Agt.

Patented Aug. 8, 1944

Plant Pat. 637

UNITED STATES PATENT OFFICE

637

ROSE PLANT

Frederick Huber Howard, Montebello, Calif.

Application December 17, 1943, Serial No. 514,702

1 Claim. (Cl. 47—61)

My present invention relates to a new and distinct variety of hybrid tea rose plants which originated from a cross between Mrs. J. D. Eisele and Condessa de Sastago. The resulting variety has been asexually reproduced and its distinguishing qualities have proved to be firmly fixed.

My new variety is exceedingly free in bloom and is practically disease-proof. The flower is camellia-like in form and is an exceedingly attractive shade of rose somewhat suffused with orange.

The illustrations making a part of this specification show three specimens of the flower of this new variety in varying stages of opening and in approximately their true colors. It must be understood, however, that this coloring is very difficult to portray with the mediums at hand.

Following is a detailed description of the plant and flower of this new variety. Color references indicate Ridgway's Color Standards and Nomenclature.

*The plant*

Growth: Vigorous and very healthy.

Form: Bushy grower, but tall. When fully developed, a total plant is composed of many separate upright bushy branches.

Blooming habits: It is a true remontant type of rose, furnishing blooms from early spring to advent of frosts. It is exceedingly free blooming, a fully developed plant producing at least 50 blooms per year.

Stems: Sturdy; upright; usually tinged with red tones, approximately Brick Red (Plate XIII); has many thorns.

*Thorns.*—Sharp; large but relatively short; slightly downward-pointing; red-tinged; irregularly spaced, sometimes bunched.

Foliage: Compound, usually with 3 to 5 leaflets.

*Size.*—Medium. Terminal leaflet approximately 2 inches long by 1½ inches wide.

*Texture.*—Leathery.

*Shape.*—Oval, with broad base and pointed apex.

*Color.*—Approximately Forest Green (Plate XVII).

Rachis: Slender and grooved above; occasional spines below.

Stipules: Clinging and very small.

Disease resistance: Practically disease-proof, particularly resistant to blackspot.

*The flower*

Bud:

*Color of small bud.*—Pomegranate Purple (Plate XII) to Carmen (Plate I).

*Color of expanding bud.*—The color is not shown in Ridgway's Color Standards and Nomenclature but would fall between Begonia Rose and Scarlet (Plate I).

*Shape.*—Oval, with broad base and pointed apex. Opening somewhat globular.

*Size.*—Five-eighths inch broad at base, about the same or slightly less in length, just before calyx breaks. When calyx breaks bud is about ¾ inch in each dimension. The half open bud is 1½ inches to 2 inches in length.

Flower:

*Size.*—Medium, 3 to 3½ inches across when fully open.

*Form.*—Beautifully and perfectly formed in loose cup-shape. This form is retained for a considerable time but later opens somewhat camellia-like. Petals reflex early.

*Petalage.*—Double, numbering about 45.

*Texture.*—Medium.

*Fragrance.*—Delightful and very pronounced.

*Color.*—The outer petals retain the coloring of the bud until the flower is fully open. The nearest in Ridgway's is Rose Doree (Plate I), but usually a little darker than that shade and suffused with Scarlet (Plate I) in the central portion of the petal. There is a large aiglet of Light Cadmium (Plate IV). The inner surface of the petals is lighter. When the rose is older and fully opened, the color changes to uniformly Deep Rose Pink (Plate XII) except that the yellow aiglet is retained.

*Shape of petals.*—Outer petals slightly longer than wide. Edge smooth. Inner petals narrower and smaller.

*Persistence of petals.*—Cling until dead.

*Lasting quality.*—Very good, flowers often lasting a full week in the cut state.

Reproductive organs:

*Pistils.*—Many; tightly bunched; set high; irregular lengths with longest in center. *Styles*—white; tipped with Red. *Stigmas*—light yellow.

*Stamens.*—Moderate number; arranged around bunched pistils. *Filaments*—red; uneven in length. *Anthers*—rather large; deep yellow (approximately Primuline Yellow (Plate XVI).

Having thus disclosed my invention, I claim:

The new and useful variety of hybrid tea rose plant, substantially as shown and described, characterized by its great resistance to disease; its vigorous upright and bushy growth; its strong leathery foliage; its exceedingly prolific production of beautifully formed flowers of very pronounced fragrance, excellent lasting qualities and pleasing, distinctive color as indicated.

FREDERICK HUBER HOWARD.